(12) United States Patent
Avery (10) Patent No.: US 11,224,107 B1
(45) Date of Patent: Jan. 11, 2022

(54) REPLACEMENT LED LIGHT BULBS WITH ULTRAVIOLET EMISSION

(71) Applicant: RETURN TO PLAY INC, Clearwater, FL (US)

(72) Inventor: Lisa M. Avery, Clearwater, FL (US)

(73) Assignee: RETURN TO PLAY INC, Clearwater, FL (US)

( * ) Notice: Subject to any disclaimer, the term of this patent is extended or adjusted under 35 U.S.C. 154(b) by 0 days.

(21) Appl. No.: 16/908,838

(22) Filed: Jun. 23, 2020

(51) Int. Cl.
*H05B 47/10* (2020.01)
*H05B 47/13* (2020.01)
*F21K 9/232* (2016.01)
*H05B 45/37* (2020.01)
*H05B 45/20* (2020.01)
*H05B 47/17* (2020.01)
*A61L 9/20* (2006.01)
*A61L 2/10* (2006.01)
*H05B 47/195* (2020.01)
*F21Y 115/10* (2016.01)

(52) U.S. Cl.
CPC ............... *H05B 47/13* (2020.01); *A61L 2/10* (2013.01); *A61L 9/20* (2013.01); *F21K 9/232* (2016.08); *H05B 45/20* (2020.01); *H05B 45/37* (2020.01); *H05B 47/17* (2020.01); *H05B 47/195* (2020.01); *A61L 2202/14* (2013.01); *A61L 2209/111* (2013.01); *A61L 2209/12* (2013.01); *F21Y 2115/10* (2016.08)

(58) Field of Classification Search
CPC ........ H05B 45/30; H05B 45/37; H05B 45/40; H05B 47/115; H05B 47/135; H05B 47/175; H05B 47/195; F21V 23/0471; A61L 2/084
See application file for complete search history.

(56) References Cited

U.S. PATENT DOCUMENTS

| 10,166,309 B2* | 1/2019 | Liao ..................... C02F 1/008 |
| 10,767,843 B2* | 9/2020 | Weeks, Jr. .......... F21V 23/0471 |
| 2005/0207152 A1* | 9/2005 | Maxik .................... H05K 1/189 362/231 |
| 2012/0319617 A1* | 12/2012 | Yen ........................ H05B 45/20 315/294 |
| 2018/0117189 A1* | 5/2018 | Yadav ...................... A61L 2/24 |
| 2018/0209609 A1* | 7/2018 | Hikmet .................... F21K 9/62 |
| 2019/0142981 A1* | 5/2019 | Kim .......................... A61L 2/10 250/455.11 |
| 2019/0247528 A1* | 8/2019 | Rodriguez ............. A61L 2/084 |

\* cited by examiner

*Primary Examiner* — Tung X Le
(74) *Attorney, Agent, or Firm* — Larson & Larson, P.A.; Frank Liebenow; Justin P. Miller (57) ABSTRACT

A sanitizing replacement LED light bulb provides visible light when powered and also provides ultraviolet light for sanitizing an area around the sanitizing LED replacement light bulb. In some embodiments, the ultraviolet light is emitted only when no motion is detected in the vicinity of the sanitizing LED replacement light bulb to prevent people and animals from being exposed to the ultraviolet light.

4 Claims, 12 Drawing Sheets

REPLACEMENT LED LIGHT BULBS WITH ULTRAVIOLET EMISSION

FIELD

This invention relates to the lighting and more particularly to replacement lighting that emit visible light, ultraviolet light, or both.

BACKGROUND

As of today, many buildings and home use florescent or incandescent lighting. Today lighting based upon light emitting diodes has become widely available and is cost competitive with existing lighting technologies, especially considering the savings in lower energy costs. Incandescent lighting utilizes more energy for the same light output, therefore incandescent lighting is more expensive when considering the energy usage over the life of various lighting technologies. Florescent lighting is more efficient than incandescent lighting and, therefore, much more cost effective, but florescent lighting has disadvantages. For one, florescent bulbs contain mercury and used bulbs must be recycled properly so as not to pollute the water tables with mercury. Another disadvantage is handling of the florescent bulb as they are often fragile and breakage leads to exposing handlers to mercury. Another disadvantage is the time it takes for a florescent bulb to emit light from the instant it is energized, as florescent bulbs are not "instant on."

In recent years, governments have limited the manufacturing and distribution of incandescent lighting. For example, in the United States, it is difficult to find an incandescent light bulb in the standard Edison format, though several smaller bulb sizes are available in incandescent format. Governments are helping to force the change to more efficient lighting technologies such as florescent and light emitting diode to reduce the burden on electricity production and, hence, reduce usage of fossil fuel in many locations.

For new construction, light emitting diode lighting (LED) technology is being designed directly into homes and buildings. As LEDs operate from voltages much lower than standard home and building service, the wiring to these integrated LED lights are often low-voltage. Further, as LEDs are generally either on (electric current is flowing) or off (electric current is not flowing), dimming is performed by duty cycle, turning the LEDs on and off very quickly so as not to be noticeable by those enjoying their light.

One problem is existing homes and buildings. Home and building owners must decide on replacing existing lighting fixtures to LED lighting fixtures or to keep the existing lighting fixtures and replace the bulbs with retrofit LED lighting having the same or similar shapes and sizes to the prior incandescent bulbs or florescent bulbs.

Homeowners often follow the replacement bulb route as existing incandescent or florescent bulbs fail and, in some instances, replace existing lighting fixtures with specialized LED lighting fixtures.

Building owners have a different issue due to the number of fixtures. Consider a high school having 5,000 florescent fixtures. The cost and down-time for replacing all of these fixtures with LED fixtures is very high. Instead, building owners often phase in LED lighting by using replacement LED bulbs, one room at a time, moving working florescent bulbs into storage for spares. Eventually, the entire building will be lit by these replacement LED bulbs.

All of the above are well known technologies, but recently, a global pandemic has struck and there is an increased need to kill pathogens in the air and on surfaces of every room. Existing lighting technology emits only visible light that has little effect on pathogens, but it has been shown that ultraviolet light is effective at killing or disabling many pathogens.

What is needed are replacement lights that emit visible light for people to be able to see and emit ultraviolet light to kill pathogens.

SUMMARY

A sanitizing LED replacement light bulb provides visible light when powered and also provides ultraviolet light for sanitizing an area around the sanitizing LED replacement light bulb. In some embodiments, the ultraviolet light is emitted only when no motion is detected in the vicinity of the sanitizing LED replacement light bulb to prevent people and animals from being exposed to the ultraviolet light.

In one embodiment, a sanitizing LED replacement lighting device is disclosed. The sanitizing LED replacement lighting device includes an enclosure with at least two terminals for receiving power from an existing lighting fixture that pass through the enclosure. There is a power conditioning circuit within the enclosure which is electrically connected to the at least two terminals. The power conditioning circuit converts the power from the existing lighting fixture into a direct current voltage potential. A plurality of visible light emitting diodes and a plurality of ultraviolet light emitting diodes are located within the enclosure. There is at least one driver within the enclosure that receives the direct current voltage potential and provides electric current to the plurality of visible light emitting diodes and the plurality of ultraviolet light emitting diodes, the plurality of visible light emitting diodes emit the visible light and the plurality of ultraviolet light emitting diodes emit the ultraviolet light. The visible light and the ultraviolet light pass through a translucent or transparent portion of the enclosure.

In another embodiment, a method of sanitizing an area around a replacement LED bulb is disclosed. The method includes providing electrical power from a fixture into which the replacement LED bulb is installed and converting the electrical power into a direct current. The method includes driving at least one visible light emitting diode with the direct current, thereby emitting visible light and driving at least one ultraviolet light emitting diode with the direct current, thereby emitting ultraviolet light.

In another embodiment, a sanitizing LED replacement lighting device is disclosed including an enclosure and a power conditioner within the enclosure. The power conditioner receives electrical power through terminals of the enclosure and converts the electrical power to direct current power. A motion detector within the enclosure is aimed outside of the enclosure for detection motion in the vicinity of the enclosure. There are a plurality of visible light emitting diodes and a plurality of ultraviolet light emitting diodes within the enclosure. A first driver circuit receives the direct current power from the power conditioner and provides a first electrical current to the plurality of visible light emitting diodes thereby the plurality of visible light emitting diodes emit the visible light and the visible light passes through a translucent or transparent portion of the enclosure. A second driver circuit receives the direct current power from the power conditioner. The second driver circuit receives a signal from the motion detector indicating whether motion is detected and the second driver circuit provides a second electrical current to the plurality of infrared light emitting diodes unless the second driver circuit receives the signal from the motion detector, thereby the plurality of ultraviolet light emitting diodes emit the ultraviolet light during an absence of motion and the ultraviolet light passes through the translucent or transparent portion of the enclosure.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments of the invention, examples of which are illustrated in the accompanying drawings. Throughout the following detailed description, the same reference numerals refer to the same elements in all figures.

The described replacement bulbs emit visible light and ultraviolet light either at different times or at the same time (overlapping). Although the embodiments shown are for certain configurations of replacement bulbs for clarity and brevity reasons, there is no limitation as to the size, shape, connection configuration, operating voltage, etc., of the disclosed replacement bulbs.

Throughout this description, the term visible light emitting diode refers to a light emitting diode that emits predominately visible light and the term ultraviolet light emitting diode refers to a light emitting diode that emits predominately ultraviolet light.

Figure 1:
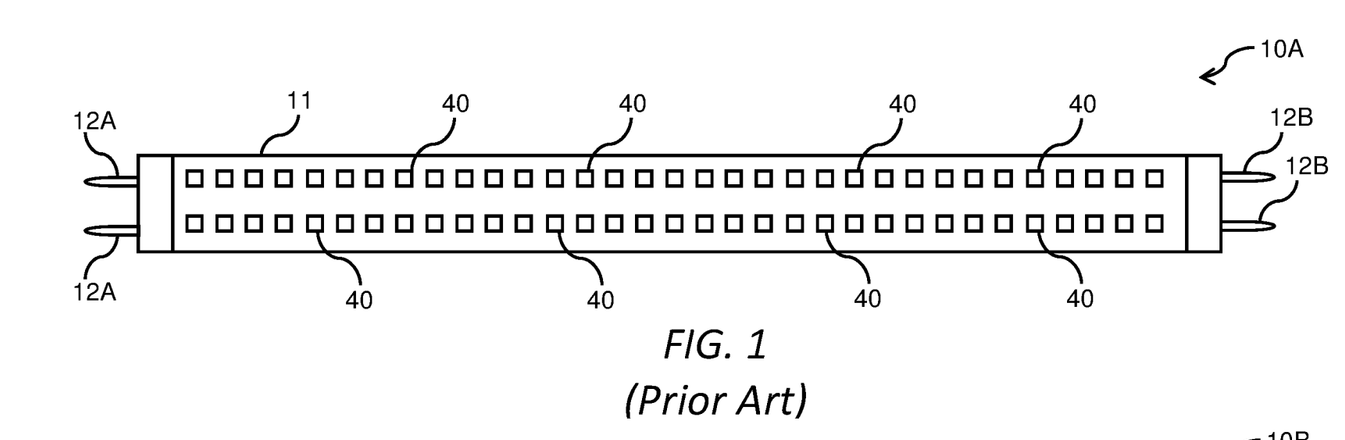
FIGS. 1-3 illustrate replacement LED lighting of the prior art consisting of multiple light emitting diodes.
Figure 2:
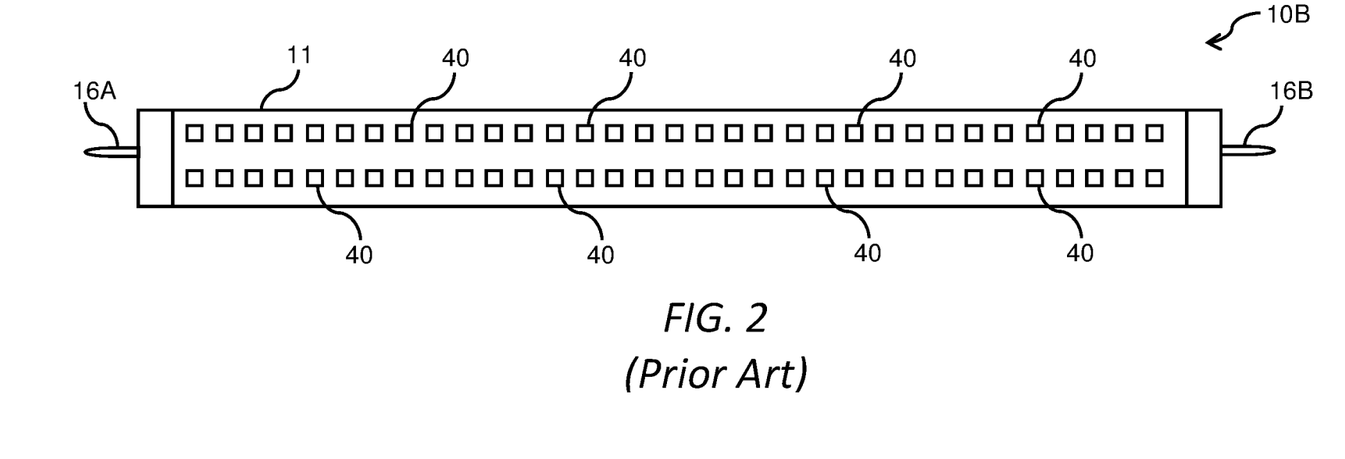
Figures 3, 4:
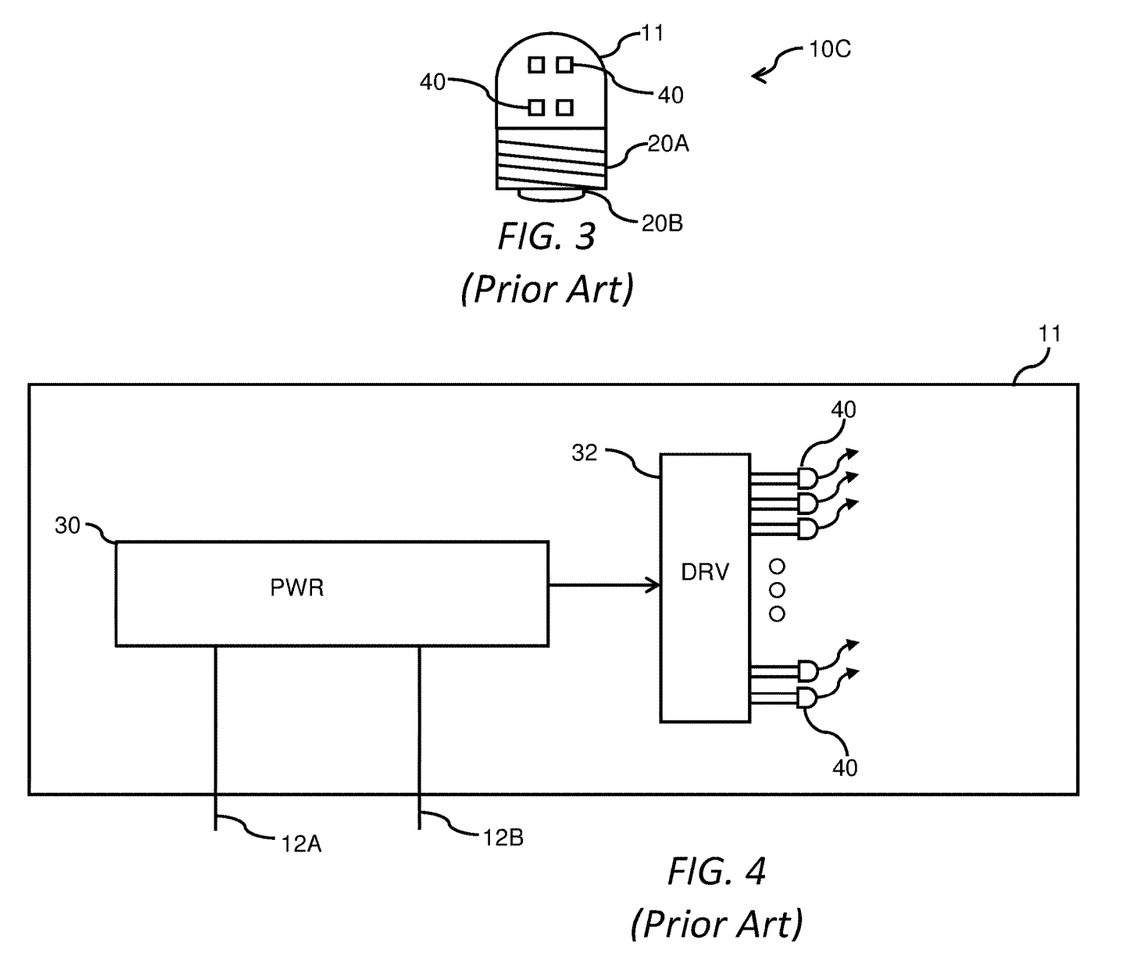
FIG. 4 illustrates a block diagram of the replacement LED lighting of the prior art consisting of multiple light emitting diodes.
Figure 5:
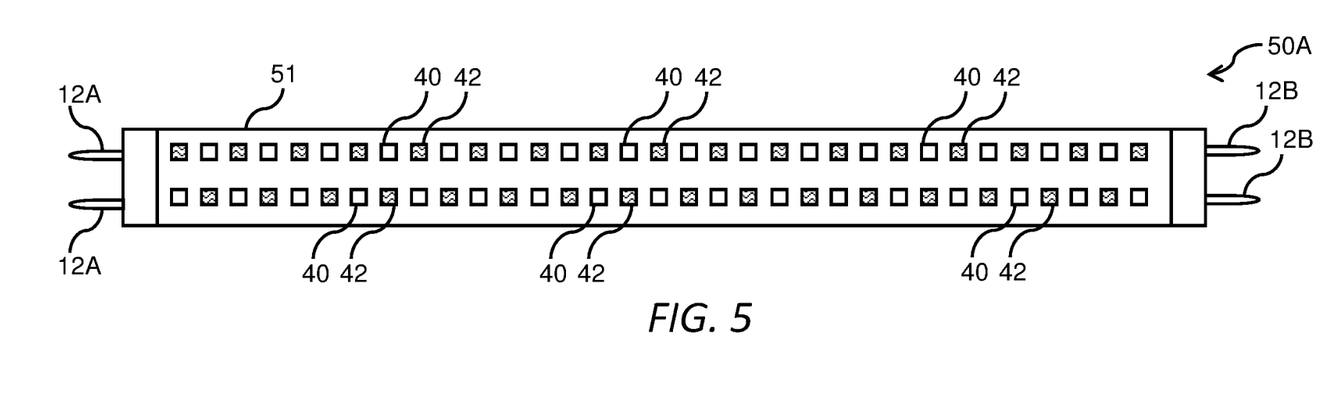
FIGS. 5-7 and 7A illustrate sanitizing LED lighting consisting of multiple light emitting diodes, some of which emit ultraviolet light.
Figure 6:
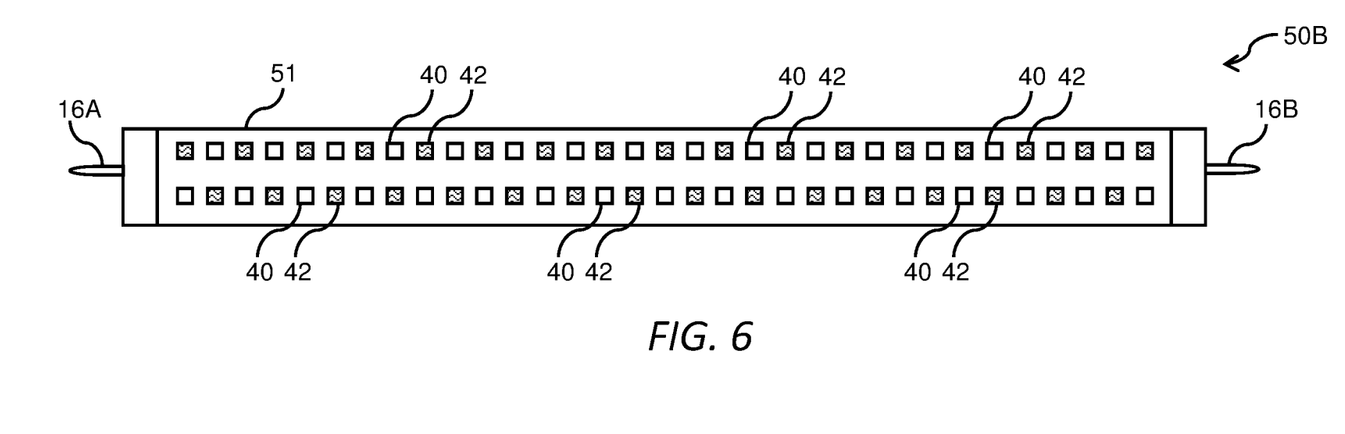
Figure 7:
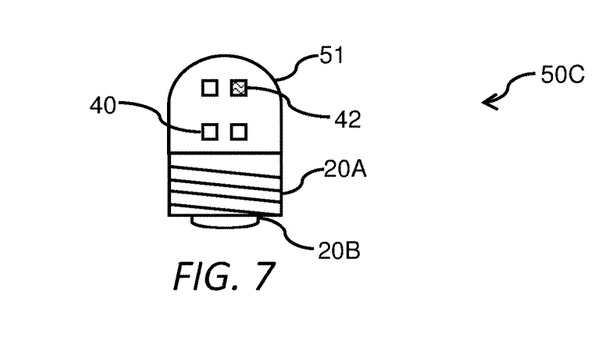
Figure 7A:
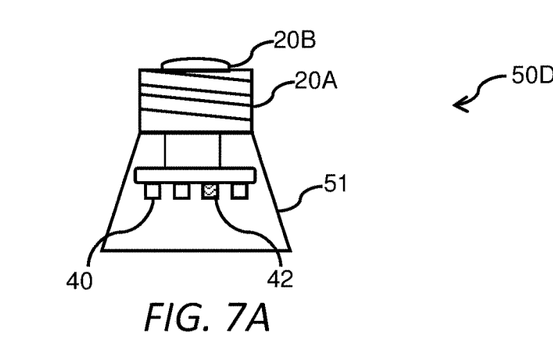

Referring to FIGS. 1-3, replacement LED lighting 10A/ 10B/10C of the prior art is shown consisting of multiple visible light emitting diodes 40. There are many shapes, sizes, configurations, and colors of LED lighting used today. In general, such replacement LED lighting 10A/106/10C has one or more visible light emitting diodes 40 packaged in an enclosure 11 that has an area that is at least partially clear or translucent to allow the visible light radiation to escape when power is applied to two or more terminals 12A/12B/ 16A/16B/20A/20B. When power is applied to the terminals 12A/12B/16A/16B/20A/20B, all of the visible light emitting diodes 40 emit visible light. In some applications, the color of each visible light emitting diode 40 is anticipated to vary so as to change the overall color temperature of the replacement LED lighting 10A/106/10C. As there are usually only two or four terminals 12A/12B/16A/16B/20A/20B and home/building wiring is generally only two-wire plus a ground, power to the replacement bulbs is either present (on) or absent (off). In some applications, dimming of the original lighting (e.g. incandescent lighting) is accomplished using standard light switch dimmers, which are often less useful for replacement LED lighting 10A/106/10C, though some replacement LED lighting 10A/106/10C is configured to operate with existing dimmers.

Referring to FIG. 4, a block diagram of the replacement LED lighting 10A/106/10C of the prior art is shown. As described above, the replacement LED lighting 10A/106/ 10C includes multiple visible light emitting diodes 40. As visible light emitting diodes 40 operate at low voltages of between 1.5 volts DC to 2 volts DC, a voltage conversion must be done within the replacement LED lighting 10A/ 106/10C as typical home/building voltages provided from existing lighting fixtures when powered is typically between 100 volts AC to 220 volts AC. In FIG. 4, such AC power enters the replacement bulbs 10 through two (or four) terminals 12A/12B and is converted to a lower voltage direct current by a power conditioning circuit 30. Each visible light emitting diode 40 or sets of visible light emitting diodes 40 are then driven by a drive circuit 32 that provides the proper voltage and current to each of the visible light emitting diodes 40. In the simplest form, the drive circuit 32 is one or more resistors that limit current to the visible light emitting diodes 40.

In operation of the replacement LED lighting 10A/106/ 10C of the prior art, when home/business power is applied to the terminals 12A/12B (e.g. a switch is turned on), the power conditioning circuit 30 provides conditioned power to the drive circuit 32 which, in turn, provides the proper voltage and current to each of the visible light emitting diodes 40.

Figure 8:
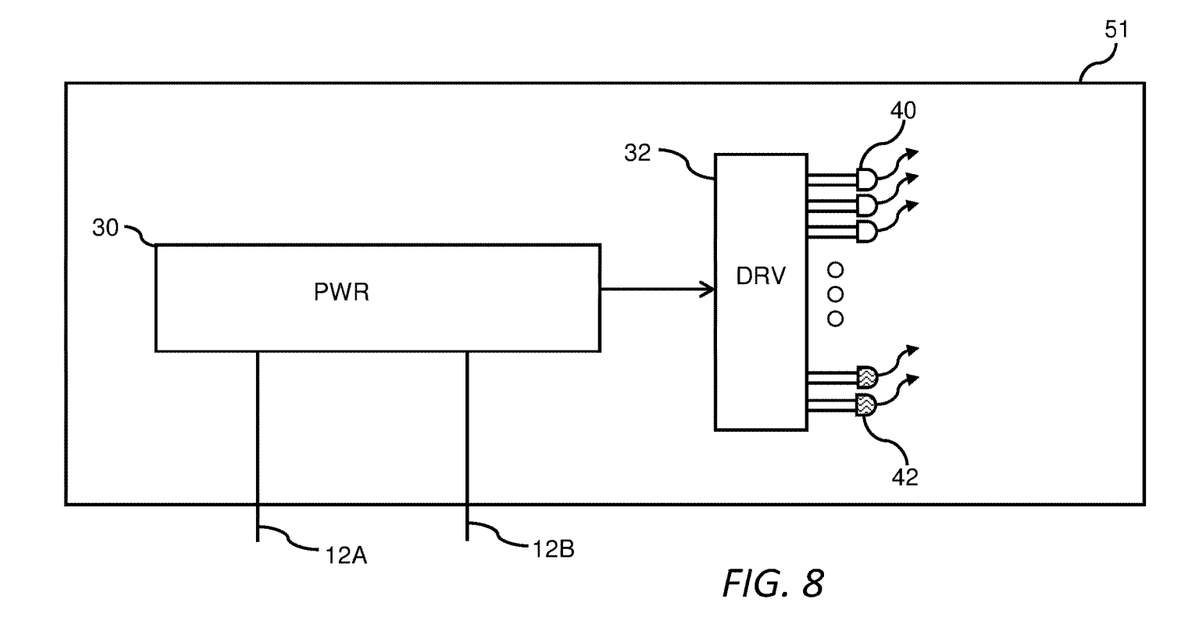
FIG. 8 illustrates a block diagram of the sanitizing replacement LED lighting consisting of multiple light emitting diodes, some of which emit ultraviolet light.

Referring to FIGS. 5-7 and 7A, sanitizing replacement LED lighting 50A/506/50C is shown consisting of multiple visible light emitting diodes 40 and one or more ultraviolet Light emitting diodes 42. There are many shapes, sizes, configurations, and colors of LED lighting anticipated, three types are shown for brevity and clarity purposes. In general, such sanitizing replacement LED lighting 50A/506/50C has one or more visible light emitting diodes 40 and one or more ultraviolet light emitting diodes 42 packaged in an enclosure 51 that has an area or bezel that is at least partially clear or translucent to allow the visible light radiation and the ultraviolet light radiation to escape when power is applied to two or more terminals 12A/12B/16A/16B/20A/20B. In the embodiment of FIG. 8, when power is applied to the terminals 12A/12B/16A/16B/20A/20B, all of the visible light emitting diodes 40 emit visible light and all of the ultraviolet light emitting diodes 42 emit ultraviolet light. In some applications, the color of each visible light emitting diode 40 is anticipated to vary so as to change the overall visible light color temperature of the sanitizing replacement LED lighting 50A/50B/50C. As there are usually only two or four terminals 12A/12B/16A/16B/20A/20B and home/building wiring is generally only two-wire plus a ground, power to the replacement bulbs is either present (on) or absent (off). In some applications, dimming of the original lighting (e.g. incandescent lighting) is accomplished using standard light switch dimmers, which are often less useful for sanitizing replacement LED lighting 50A/50B/50C, though some sanitizing replacement LED lighting 50A/50B/50C is anticipated to have circuitry that will operate with existing dimmers.

Referring to FIG. 8, a block diagram of the sanitizing replacement LED lighting 50. As described above, the sanitizing replacement LED lighting 50 includes multiple visible light emitting diodes 40 and one or more ultraviolet Light emitting diodes 42. As visible light emitting diodes 40 and ultraviolet Light emitting diodes 42 operate at low voltages of between 1.5 volts DC to 2 volts DC, a voltage conversion must be done within the sanitizing replacement LED lighting 50 as typical home/building voltages provided from existing lighting fixtures when powered is typically between 100 volts AC to 220 volts AC. In FIG. 8, such AC power enters the replacement bulbs 10 through two (or four) terminals 12A/12B and is converted to a lower voltage direct current by a power conditioning circuit 30. Each visible light emitting diodes 40 or sets of visible light emitting diodes 40 and ultraviolet Light emitting diode 42 or sets of ultraviolet Light emitting diodes 42 are then driven by a drive circuit 32 that provides the proper voltage and current to each of the visible light emitting diodes 40 and to each of the ultraviolet Light emitting diodes 42. In the simplest form, the drive circuit 32 is one or more resistors that limit current to the visible light emitting diodes 40 and to the ultraviolet Light emitting diodes 42.

In operation of the sanitizing replacement LED lighting 50, when home/business power is applied to the terminals 12A/12B (e.g. a switch is turned on), the power conditioning circuit 30 provides conditioned power to the drive circuit 32 which, in turn, provides the proper voltage and current to each of the visible light emitting diodes 40 and to each of the ultraviolet Light emitting diodes 42.

Figure 9:
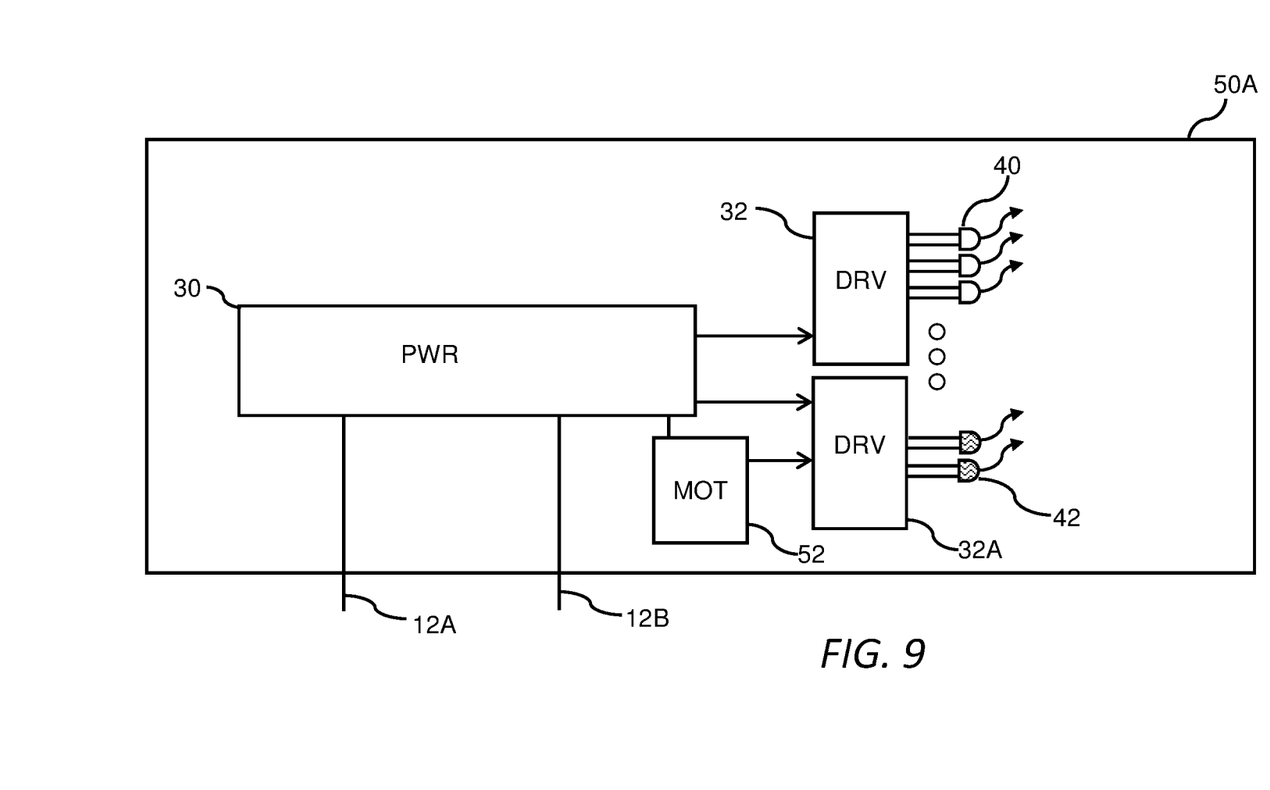
FIGS. 9 and 10 illustrate block diagrams of the sanitizing replacement LED lighting with motion detection and consisting of multiple light emitting diodes, some of which emit ultraviolet light.
Figure 10:
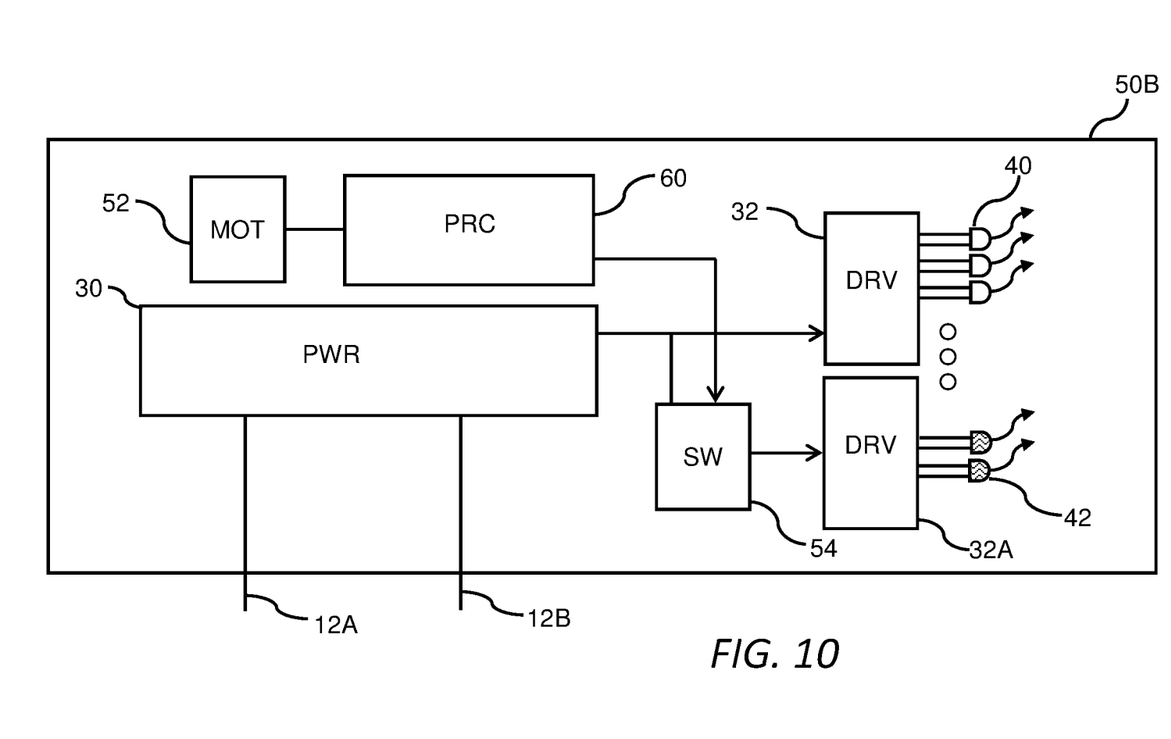

Referring to FIGS. 9 and 10, block diagrams of the sanitizing replacement LED lighting 50A/50B with motion detection are shown. As described above, the sanitizing replacement LED lighting 50A/50B includes multiple visible light emitting diodes 40 and one or more ultraviolet Light emitting diodes 42. As visible light emitting diodes 40 and ultraviolet Light emitting diodes 42 operate at low voltages of between 1.5 volts DC to 2 volts DC, a voltage conversion must be done within the sanitizing replacement LED lighting 50A/50B as typical home/building voltages provided from existing lighting fixtures when powered is typically between 100 volts AC to 220 volts AC. In FIGS. 9 and 10, such AC power enters the sanitizing replacement LED lighting 50A/50B through two (or four) terminals 12A/12B and is converted to a lower voltage direct current by a power conditioning circuit 30. The visible light emitting diodes 40 or sets of visible light emitting diodes 40 are then driven by a drive circuit 32 that provides the proper voltage and current to each of the visible light emitting diodes 40. The ultraviolet light emitting diodes 42 or sets of ultraviolet light emitting diodes 42 are driven by a second driver circuit 32A that provides the proper voltage and current to each of the ultraviolet light emitting diodes 42. In the simplest form, the drive circuits 32/32A are one or more resistors that limit current to the visible light emitting diodes 40 and to the ultraviolet Light emitting diodes 42.

In the embodiment of FIG. 9, the sanitizing replacement LED lighting 50A includes a motion detector 52 that receives power from the power conditioning circuit 30 and is operationally connected to the second driver circuit 32A. When there is motion in the vicinity of the sanitizing replacement LED lighting 50A, the motion detector 52 detects such motion and presents an inhibit signal to the second driver circuit 32A. Upon receiving the inhibit signal, the second driver circuit 32A prevents the flow of current through the ultraviolet light emitting diodes 42, therefore inhibiting emission of ultraviolet light.

In operation of the sanitizing replacement LED lighting 50A, when home/business power is applied to the terminals 12A/12B (e.g. a switch is turned on), the power conditioning circuit 30 provides conditioned power to the drive circuit 32 which, in turn, provides the proper voltage and current to each of the visible light emitting diodes 40. After which, when there is no motion detected by the motion detector 52, the second driver circuit 32A provides the proper voltage and current to each of the ultraviolet Light emitting diodes 42.

In the embodiment of FIG. 10, the sanitizing replacement LED lighting 50B includes a processor 60 to which a motion detector 52 is interfaced. Power is again provided by the power conditioning circuit 30. When there is motion in the vicinity of the sanitizing replacement LED lighting 50B, the motion detector 52 detects such motion and presents an indication of movement signal to the processor. When there is no movement detected by the motion detector 52, the processor signals a power switch 54 (e.g. a solid-state switch) to provide power from the power conditioning circuit 30 to the second driver circuit 32A. When there is movement detected by the motion detector 52, the processor controls the power switch 54 to disable the flow of power to the second driver circuit 32A, thereby preventing emission of ultraviolet light by preventing the flow of electric current through the ultraviolet light emitting diodes 42.

In operation of the sanitizing replacement LED lighting 50B, when home/business power is applied to the terminals 12A/12B (e.g. a switch is turned on), the power conditioning circuit 30 provides conditioned power to the drive circuit 32 which, in turn, provides the proper voltage and current to each of the visible light emitting diodes 40. After which, when there is no motion detected by the motion detector 52, the processor signals the power switch 54 to provide power to the second driver circuit 32A, which in turn, provides the proper voltage and current to each of the ultraviolet Light emitting diodes 42 thereby emitting ultraviolet light.

Figure 11:
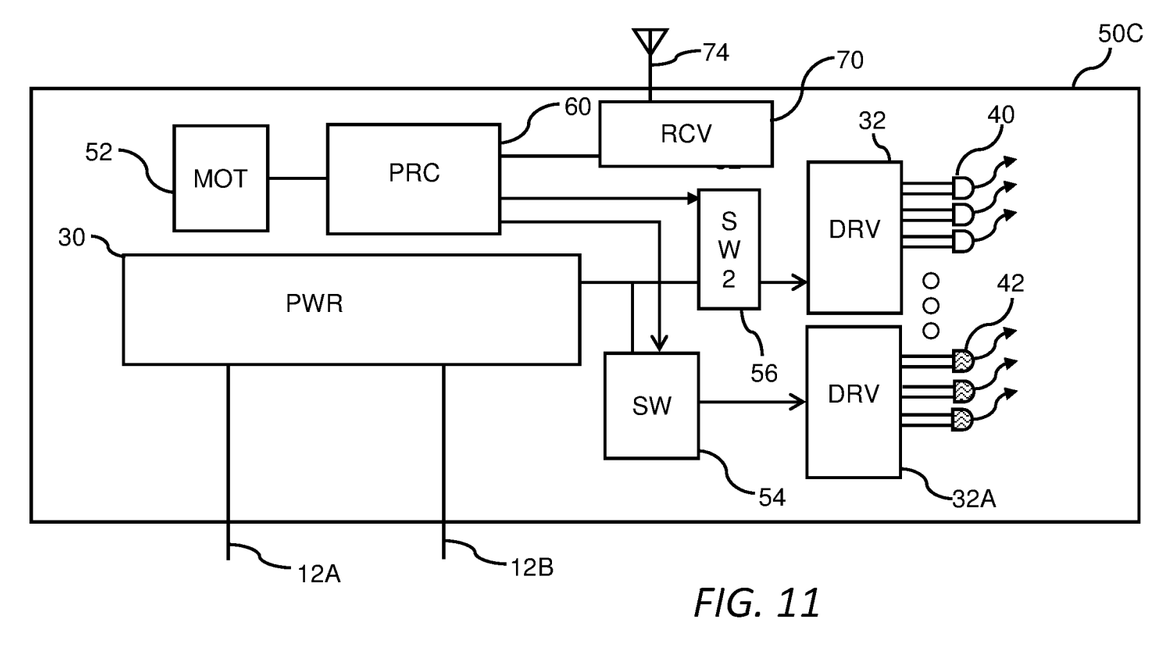
FIG. 11 illustrates a block diagram of the sanitizing replacement LED lighting with remote control consisting of multiple light emitting diodes, some of which emit ultraviolet light.

Referring to FIG. 11, a block diagram of the sanitizing replacement LED lighting 50C with remote control capabilities is shown. As described above, the sanitizing replacement LED lighting 50C includes multiple visible light emitting diodes 40 and one or more ultraviolet light emitting diodes 42. As visible light emitting diodes 40 and ultraviolet Light emitting diodes 42 operate at low voltages of between 1.5 volts DC to 2 volts DC, a voltage conversion must be done within the sanitizing replacement LED lighting 50A/50B as typical home/building voltages provided from existing lighting fixtures when powered is typically between 100 volts AC to 220 volts AC. In FIGS. 9 and 10, such AC power enters the sanitizing replacement LED lighting 50C through two (or four) terminals 12A/12B and is converted to a lower voltage direct current by a power conditioning circuit 30. The visible light emitting diodes 40 or sets of visible light emitting diodes 40 are then driven by a drive circuit 32 that provides the proper voltage and current to each of the visible light emitting diodes 40. The ultraviolet light emitting diodes 42 or sets of ultraviolet light emitting diodes 42 are driven by a second driver circuit 32A that provides the proper voltage and current to each of the ultraviolet light emitting diodes 42. In the simplest form, the drive circuits 32/32A are one or more resistors that limit current to the visible light emitting diodes 40 and to the ultraviolet Light emitting diodes 42.

In the embodiment of FIG. 11, the sanitizing replacement LED lighting 50C includes a processor 60, a wireless receiver 70, and a motion detector 52 (optional) that receive power from the power conditioning circuit 30. In this way, the processor 60 receives signals from the wireless receiver 70 for controlling operation of the sanitizing replacement LED lighting 50C.

In some embodiments, the wireless receiver 70 receives radio frequency signals from a wireless remote control 8 (see FIG. 15) by way of an antenna 74 while in other embodiments, the wireless receiver 70 receives radio frequency signals from a wireless remote control 8 by way of a light sensor (not shown). Receiving signals from the wireless receiver 70, the processor determines which light emitting diodes 40/42 are to be energized and has the ability to control the brightness of those light emitting diodes 40/42 that are energized by controlling a power switch 54 for the visible light emitting diodes 40 and a second power switch 56 for the ultraviolet light emitting diodes 42. Note that this is an example of how the processor 60 controls power to the visible light emitting diodes 40 and the ultraviolet light emitting diodes 42 as there are many control mechanisms anticipated, all of which are included here within.

In embodiments having a motion detector 52, if there is motion in the vicinity of the sanitizing replacement LED lighting 50C, the motion detector 52 detects such motion and signals the processor 60. The processor then signals the power switch 54 to inhibit power to the second driver circuit 32A, thereby preventing emission of ultraviolet light while motion is detected. Note that by having a processor 60 (or equivalent logic), the sanitizing replacement LED lighting 50C has the ability to include hysteresis in signaling the power switch 54. For example, once the motion is no longer detected, the processor 60 maintains the signal to the power switch 54 to inhibit power to the second driver circuit 32A for a period of time to allow for any person or animal to vacate the area around the sanitizing replacement LED lighting 50C.

In operation of the sanitizing replacement LED lighting 50C, it is anticipated that home/business power is constantly applied to the terminals 12A/12B and the power conditioning circuit 30 continuously provides conditioned power to the processor 60, the wireless receiver 70, and the motion detector 52 (optional). Under control of the processor, the proper voltage and electrical current is provided to each of the visible light emitting diodes 40 when controlled by a wireless remote control 8. In some embodiments, when there is no motion detected by the motion detector 52, the processor instructs the second power switch 56 to provide power to the second driver circuit 32A, thereby providing the proper voltage and current to each of the ultraviolet light emitting diodes 42.

Figure 12:
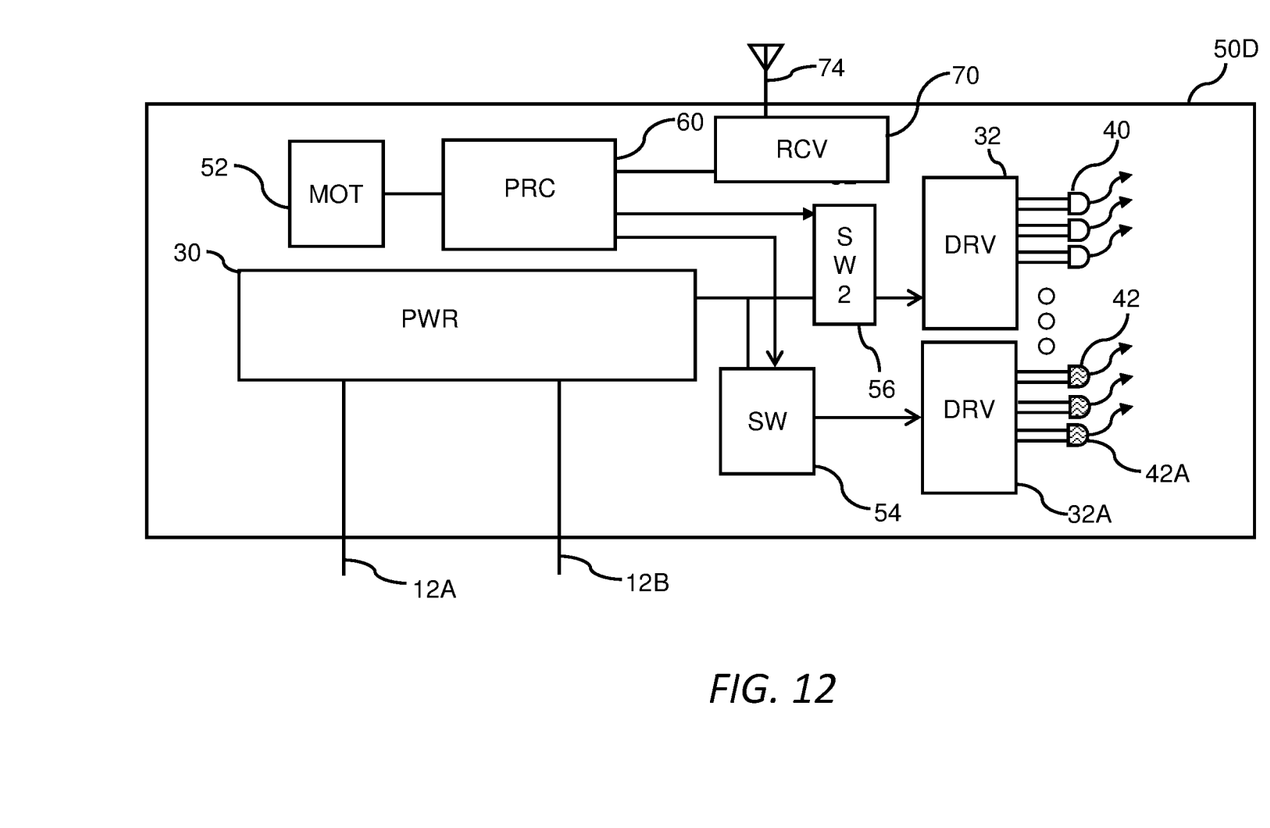
FIG. 12 illustrates a block diagram of the sanitizing replacement LED lighting with remote control and indication of ultraviolet emission having multiple light emitting diodes, some of which emit ultraviolet light.

Referring to FIG. 12, an alternate block diagram of the replacement LED lighting 50D with remote control capabilities is shown. This embodiment is similar to that shown in FIG. 11 with one minor difference, that being that the light emitting diodes that are driven by the second driver circuit 32A includes ultraviolet light emitting diodes 42 and one or more indication visible light emitting diodes 42A (e.g. blue light emitting diodes) that signal any person that is in the vicinity of the replacement LED lighting 50D that ultra violet light is being emitted. When the processor 60 signals the power switch 54 to provide power to the second driver circuit 32A, the second driver circuit 32A drives current through one or more indication visible light emitting diodes 42A, thereby emitting visible light of a specific color or colors to warn those in the vicinity of the replacement LED lighting 50D that ultra violet light is being emitted.

Figure 13:
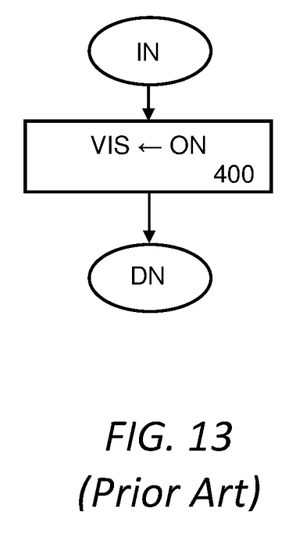
FIG. 13 illustrates a flow chart of the replacement LED lighting of the prior art.

Referring to FIG. 13, flow chart of the replacement LED lighting of the prior art is shown. In this, upon power being provided, the visible light emitting diodes 40 are illuminated 400.

Figure 14:
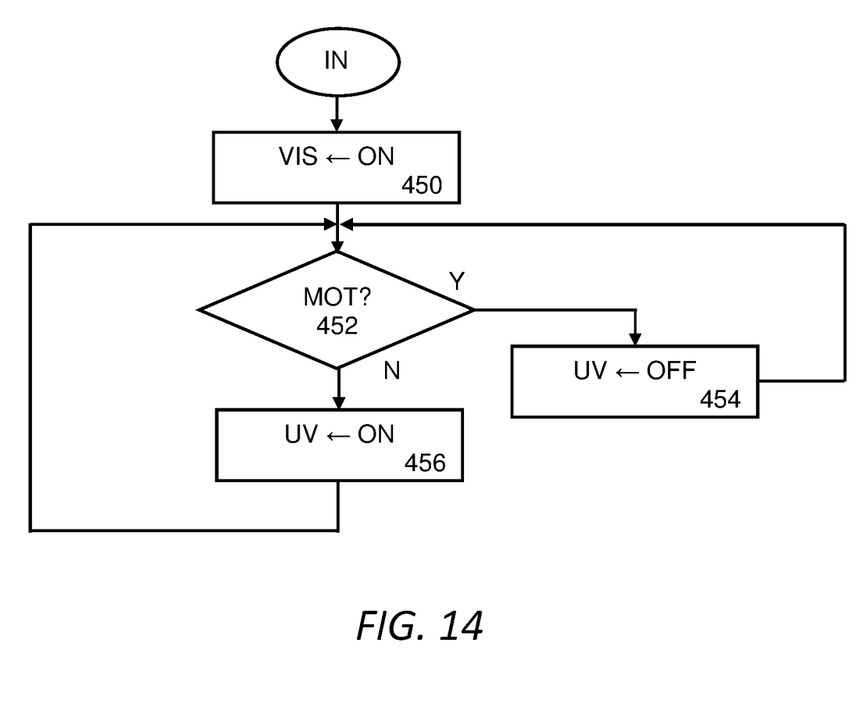
FIG. 14 illustrates a flow chart of the sanitizing replacement LED lighting with motion detection.

Referring to FIG. 14, a flow chart of the sanitizing replacement LED lighting 50A with motion detection is shown. In this flow chart, upon power being provided, the visible light emitting diodes 40 are illuminated 450. Next a loop begins (as long as power is provided to the sanitizing replacement LED lighting 50A with motion detection). In the loop, it is determined if there is motion 452 in the vicinity of the sanitizing replacement LED lighting 50A with motion detection. If there is motion 452, the one or more ultraviolet Light emitting diodes 42 are shut off or remain off and no ultraviolet light (or minimal ultraviolet light) is emitted. If there is motion 452, the one or more ultraviolet Light emitting diodes 42 are turned on or remain on and ultraviolet light is emitted for sanitizing the area around the sanitizing replacement LED lighting 50A with motion detection.

Figure 15:
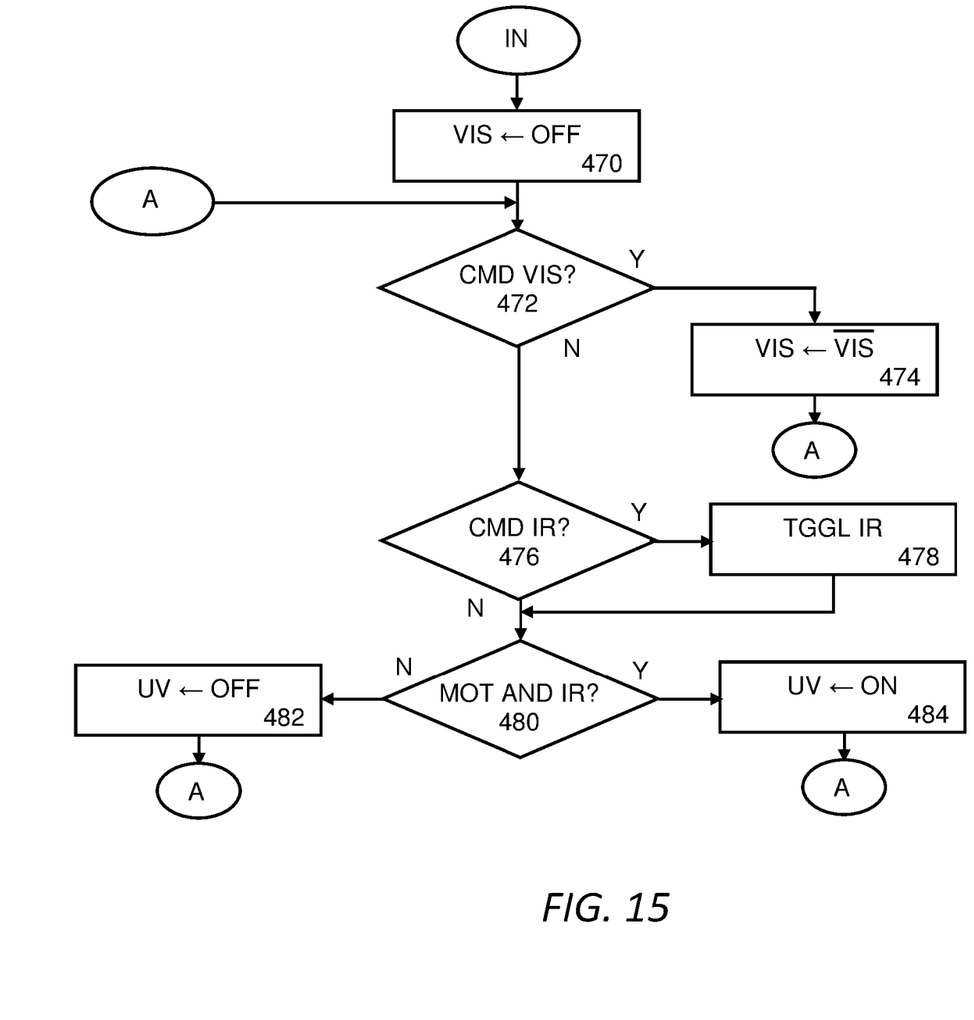
FIG. 15 illustrates a flow chart of the sanitizing replacement LED lighting with motion detection and remote control.

FIG. 15 illustrates a flow chart of the sanitizing replacement LED lighting 50C with motion detection and remote control. In this flow chart, upon power being provided, the visible light emitting diodes 40 are illuminated 470. Next a loop (A) begins (as long as power is provided to the sanitizing replacement LED lighting 50C with motion detection and remote control). In the loop, it is determined if a command has been received to turn on/off 472 the visible lighting of the sanitizing replacement LED lighting 50C. If the command has been received to turn on/off 472, the visible light emitting diodes 40 are controlled 474 to illuminate (current flows through the visible light emitting diodes 40) if previously off or the visible light emitting diodes 40 are controlled to extinguish (current does not flow through the visible light emitting diodes 40) if previously on.

Next, it is determined if a command has been received to toggle 476 operation of the motion detector and if the command has been received to toggle 476 operation of the motion detector, the operation of the motion detector is toggled 478 (changed back and forth between enabled and disabled).

Now, it is determined if the operation of the motion detector is enabled 480 (IR) and if the operation of the motion detector is enabled 480 (IR) and there is motion 452 in the vicinity of the replacement LED lighting 50A with motion detection, the one or more ultraviolet Light emitting diodes 42 are shut off or remain off and no ultraviolet light (or minimal ultraviolet light) is emitted. If there is no motion 452 or the motion detector is disabled 480 (IR), the one or more ultraviolet Light emitting diodes 42 are turned on or remain on and ultraviolet light is emitted for sanitizing the area around the replacement LED lighting 50A with motion detection.

Figure 16:
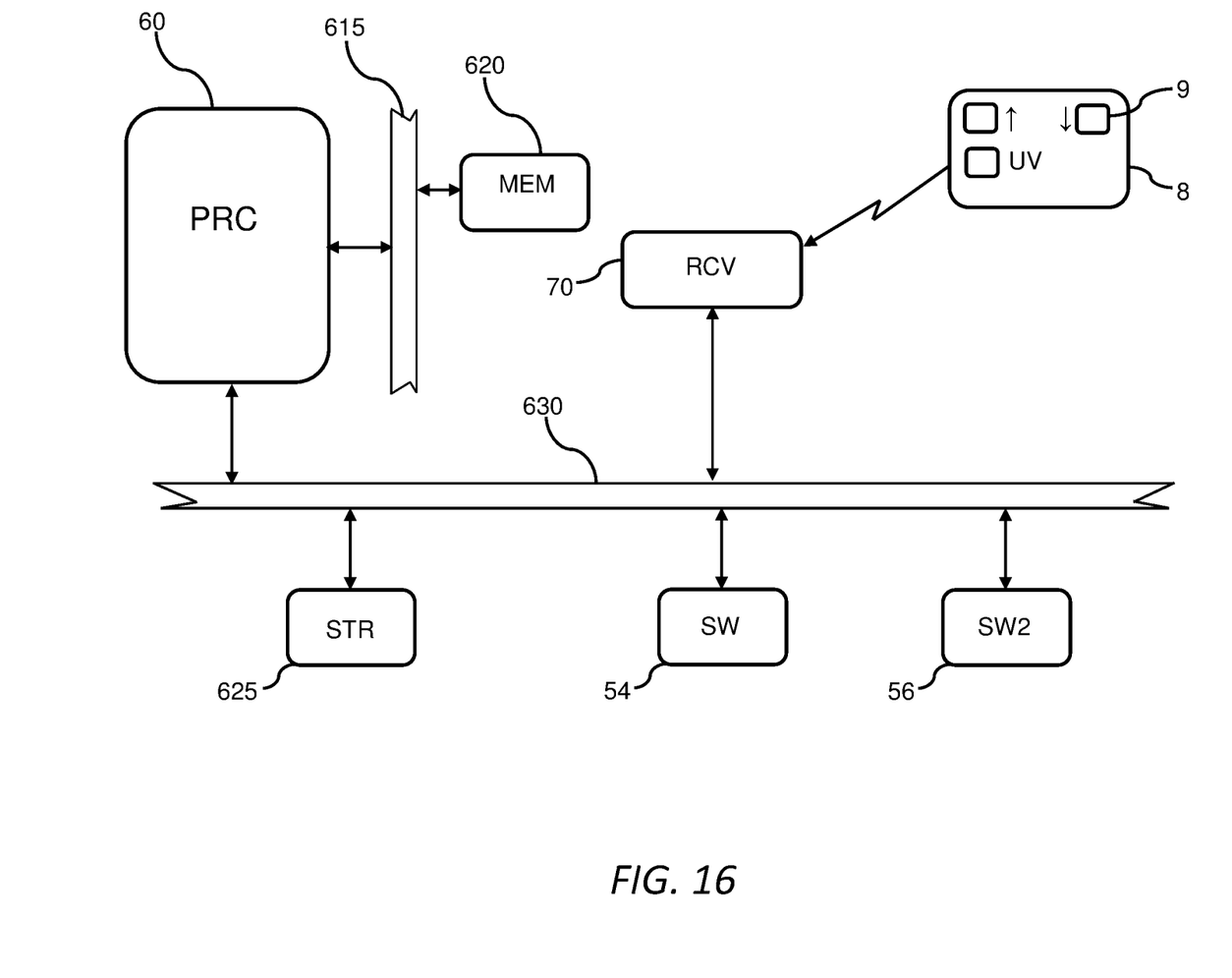
FIG. 16 illustrates a schematic view of an exemplary sanitizing replacement LED lighting with motion detection and remote control.

Referring to FIG. 16, a schematic view of an exemplary system of the sanitizing replacement LED lighting 50C with motion detection and remote control is shown. The example system represents an exemplary processor-based system. Although, a processor-based system is described, it is known to implement the same or similar functionality in a system of logic or analog components providing similar functionality in an equivalent system.

The sanitizing replacement LED lighting 50C as shown in its simplest form has a single processor 60 (e.g., controller, microcontroller, microprocessor, etc.). Many different computer architectures are known that accomplish similar results in a similar fashion and the present invention is not limited in any way to any particular processor 60. In exemplary systems, the processor 60 executes or runs stored programs that are generally stored for execution within a memory 620. The memory 620 is connected to the processor by a memory bus 615 and is any memory 620 suitable for connection with the processor 60, such as SRAM, DRAM, SDRAM, RDRAM, DDR, DDR-2, etc. Also connected to the processor 60 is a system bus 630 for connecting to peripheral subsystems. A non-transitory secondary storage 625 is interfaced to the processor 60 through the system bus 630 and is used to store programs, executable code and data persistently. Examples of non-transitory secondary storage 625 include battery-backed semiconductor memory, flash memory, etc.

The processor 60 communicates with one or more power switching circuits 54/56, each controlling a flow of electrical current through one or more visible light emitting diodes 40 or ultraviolet light emitting diodes 42.

In some embodiments, the processor 60 is interfaced to a wireless receiver 70 for receiving commands from a wireless remote control 8. The wireless receiver receives either radio waves (RF) or light waves (IR) from the wireless remote control 8 in response to one or more remote control switches 9 (e.g. buttons) being operated. For example, if the remote control switch 9 labeled "down" (down arrow) is operated, an encoded wireless transmission is sent from the wireless remote control 8 to the wireless receiver. The processor 60 receives this command from the wireless receiver 70 and responsive to such, communicates with one or more power switching circuits 54/56 to reduce the flow of electrical current through the one or more visible light emitting diodes 40. If the remote control switch 9 labeled "up" (up arrow) is operated, a different encoded wireless transmission is sent from the wireless remote control 8 to the wireless receiver. The processor 60 receives this command from the wireless receiver 70 and responsive to such, communicates with one or more power switching circuits 54/56 to increase the flow of electrical current through the one or more visible light emitting diodes 40.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A sanitizing replacement LED lighting device comprising:
    an enclosure;
    a power conditioner within the enclosure, the power conditioner receives electrical power through terminals of the enclosure and converts the electrical power to direct current power;
    a motion detector within the enclosure and aimed outside of the enclosure is for detecting of motion in the vicinity of the enclosure;
    a plurality of visible light emitting diodes within the enclosure;
    a plurality of ultraviolet light emitting diodes within the enclosure;
    a first driver circuit within the enclosure, the first driver circuit receives the direct current power from the power conditioner and provides a first electrical current to the plurality of visible light emitting diodes thereby the plurality of visible light emitting diodes emit visible light and the visible light passes through a translucent or transparent portion of the enclosure; and
    a second driver circuit within the enclosure, the second driver circuit receives the direct current power from the power conditioner, the second driver circuit receives a signal from the motion detector indicating motion is detected, the second driver circuit provides a second electrical current to the plurality of ultraviolet light emitting diodes unless the second driver circuit receives the signal from the motion detector thereby the plurality of ultraviolet light emitting diodes emit the ultraviolet light during an absence of motion and the ultraviolet light passes through the translucent or transparent portion of the enclosure.

2. The sanitizing replacement LED lighting device of claim 1, wherein the power conversion circuit converts supply alternating current into the direct current power.

3. The sanitizing replacement LED lighting device of claim 1, wherein the enclosure includes a transparent or translucent bezel through which light from the plurality of visible light emitting diodes and light from the plurality of ultraviolet light emitting diodes escapes from the enclosure.

4. The sanitizing replacement LED lighting device of claim 1, wherein the motion detector is an infrared motion detector.

* * * * *